United States Patent [19]

Nogami et al.

[11] 4,299,486
[45] Nov. 10, 1981

[54] SPECTROFLUOROMETER

[75] Inventors: Taro Nogami; Hiroshi Hirose, both of Ibaraki, Japan

[73] Assignee: Hitachi, Ltd., Tokyo, Japan

[21] Appl. No.: 118,725

[22] Filed: Feb. 5, 1980

[30] Foreign Application Priority Data

Feb. 16, 1979 [JP] Japan .................................. 54/16793

[51] Int. Cl.³ ............................................. G01N 21/64
[52] U.S. Cl. ................................... 356/318; 250/461 R
[58] Field of Search ............... 356/317, 318, 365, 367; 250/458, 459, 461 R, 461 B

[56] References Cited

U.S. PATENT DOCUMENTS

| | | | |
|---|---|---|---|
| 3,092,722 | 6/1963 | Howerton | 250/461 R X |
| 3,679,309 | 7/1972 | Hiragaki et al. | 356/317 X |
| 3,971,952 | 7/1976 | Inbar et al. | 250/461 B |
| 4,074,939 | 2/1978 | Rabl | 356/364 X |
| 4,203,670 | 5/1980 | Bromberg | 356/367 |

Primary Examiner—F. L. Evans
Attorney, Agent, or Firm—Craig and Antonelli

[57] ABSTRACT

In order to provide a spectrofluorometer which measures the emission polarization spectrum of a sample at high precision and with ease, a first spectrum signal $I_{HV}(\lambda_{EM})$ and a second spectrum signal $I_{HH}(\lambda_{EM})$ are formed by scanning the wavelength of an emission monochromator. A third spectrum signal $I_{VH}(\lambda_{EM})$ and a fourth spectrum signal $I_{VV}(\lambda_{EM})$ are also formed. In these terms, the first suffix H of the signals means that excitation light irradiated at the sample has a horizontal polarization direction while the first suffix V of the signals means that excitation light irradiated at the sample has a vertical polarization direction. The second suffix H of the signals means that fluorescence light detected by the detector has a horizontal polarization direction. The second suffix V of the signal means that fluorescence light detected by the detector has a vertical polarization direction. Using these signals the spectrofluorometer produces a signal $G(\lambda_{EM})$ representative of the ratio between the signal $I_{HV}(\lambda_{EM})$ and the signal $I_{HH}(\lambda_{EM})$. Also, a correction signal $G(\lambda_{EM}) \cdot I_{VH}(\lambda_{EM})$ is formed of the ratio signal $G(\lambda_{EM})$ and the third spectrum signal $I_{VH}(\lambda_{EM})$. Then, a signal $I_{VV}(\lambda_{EM}) - G(\lambda_{EM}) \cdot I_{VH}(\lambda_{EM})$ representative of the difference between the correction signal $G(\lambda_{EM}) \cdot I_{VH}(\lambda_{EM})$ and the fourth spectrum signal $I_{VV}(\lambda_{EM})$ is divided by a signal $I_{VV}(\lambda_{EM}) + G(\lambda_{EM}) \cdot I_{VH}(\lambda_{EM})$ representative of the sum between them. The resulting signal $$\frac{I_{VV}(\lambda_{EM}) - G(\lambda_{EM}) \cdot I_{VH}(\lambda_{EM})}{I_{VV}(\lambda_{EM}) + G(\lambda_{EM}) \cdot I_{VH}(\lambda_{EM})}$$

is indicated as the emission polarization spectrum by the spectrofluorometer.

7 Claims, 4 Drawing Figures

SPECTROFLUOROMETER

BACKGROUND OF THE INVENTION

This invention relates to a spectrofluorometer, and more particularly to a spectrofluorometer which can measure an emission polarization spectrum precisely and simply.

The polarization measurement which has been carried out in a prior-art spectrofluorometer affords an excitation polarization spectrum. More specifically, an excitation spectrum signal $I_{VV}(\lambda_{EX})$ is obtained by performing the wavelength scanning of an excitation monochromator under the conditions under which an emission wavelength is fixed and under which the polarization direction of an excitation polarizer is set to be vertical, while the polarization direction of an emission polarizer is set to be vertical. An excitation spectrum signal $I_{VH}(\lambda_{EX})$ is obtained by performing the wavelength scanning of the excitation monochromator with the polarization direction of the excitation polarizer set vertical and the polarization direction of the emission polarizer set horizontal. From these excitation spectrum signals, the excitation polarization spectrum $P(\lambda_{EX})$ is found in conformity with the following expression:

$$P(\lambda_{EX}) = \frac{I_{VV}(\lambda_{EX}) - G \cdot I_{VH}(\lambda_{EX})}{I_{VV}(\lambda_{EX}) + G \cdot I_{VH}(\lambda_{EX})}$$

where G denotes the grating correction factor for correcting the polarization characteristics of an emission monochromator dependent upon the measurement wavelength. The factor G is obtained from the following expression:

$$G = I_{HV}/I_{HH}$$

The evaluation of the factor G is executed by operations described hereunder, by exploiting the fact that when excitation light is polarized in the horizontal direction, fluorescence observed on a horizontal plane in a direction of 90 degrees relative to the excitation light is not polarized.

The emission or fluorescence intensity signal $I_{HH}$ is measured at the time when, at the emission wavelength (fixed) for use in the measurement, the polarization direction of the excitation polarizer is made horizontal and that of the emission polarizer is made horizontal. Subsequently, the emission intensity signal $I_{HV}$ is measured at the time when, at the same emission wavelength, the polarization direction of the excitation polarizer is made horizontal and that of the emission polarizer is made vertical. The grating correction factor G for correcting the polarization characteristics of the emission monochromator at the emission wavelength used in the measurement is obtained from these signals $I_{HH}$ and $I_{HV}$.

As described above, in the prior-art spectrofluorometer, the excitation polarization spectrum is measured under the condition that the emission wavelength is constant, in other words, that the polarization characteristics of the emission monochromator are constant. A change in the emission wavelength results in changing the grating correction factor G accordingly.

On the other hand, the advent of a spectrofluorometer which can measure not only the excitation polarization spectrum but also an emission polarization spectrum has been wished for owing to the desire of investigating properties inherent to a substance from various angles. The reason is that samples on which the properties inherent to the substance cannot be qualitatively grasped merely by the measurement of the excitation polarization spectrum have been often met with.

The measurement of the emission polarization spectrum is carried out by fixing an excitation wavelength instead of fixing the emission wavelength in the measurement of the excitation polarization spectrum and by scanning the emission wavelength instead of scanning the excitation wavelength. Accordingly, a problem in the case of measuring the emission polarization spectrum with the prior-art apparatus is that the scanning of the emission wavelength causes the grating correction factor G for correcting the polarization characteristics of the emission monochromator dependent upon the measurement wavelength, to vary depending upon the scanning wavelength. It requires much labor and a long time to evaluate the grating correction factor G at various wavelength positions of the scanning wavelength. Therefore, the emission polarization spectrum has been obtained without considering the grating correction factor G, or the measurement of the emission polarization spectrum has been given up. The emission polarization spectrum obtained without taking the grating correction factor G into account cannot be said the true emission polarization spectrum, and its precision being too low has made it impossible to be supplied to the qualitative analysis.

SUMMARY OF THE INVENTION

An object of this invention is to provide a spectrofluorometer which is capable of a wide range of analyses at high precision.

Another object of this invention is to provide a spectrofluorometer which can simply measure an emission polarization spectrum at high precision.

Another object of this invention is to provide a spectrofluorometer which can promptly measure an emission polarization spectrum.

Another object of this invention is to provide a spectrofluorometer which affords an emission polarization spectrum with the influence of an apparatus function compensated for.

Another object of this invention is to provide a spectrofluorometer which can easily analyze the intermolecular energy transfer.

The objects of this invention can be accomplished by a spectrofluorometer comprising a light source; first spectroscopic means to separate light from said light source into its spectral components; a fluorescent sample which is excited by monochromatic light from said first spectroscopic means and which emits fluorescence; first polarization means arranged between said first spectroscopic means and said fluorescent sample and adapted to transmit monochromatic light having a polarization component in a specified direction among the monochromatic light components from said first spectroscopic means; second spectroscopic means to separate the fluorescence emitted from said fluorescent sample, into its spectral components; second polarization means arranged between said fluorescent sample and said second spectroscopic means and adapted to transmit fluorescence having a polarization component in a specified direction among the fluorescence components emitted from said fluorescent sample; sensing means to sense light emergent from said second spectroscopic means; wavelength drive means to selectively vary wavelengths of lights emergent from said first and second spectroscopic means; means to form a ratio between a first spectrum signal and a second spectrum signal, said first spectrum signal being obtained as a function of the wavelength by continuously varying the wavelength of the light emergent from said second spectroscopic means when polarization directions of said first and second polarization means are set identical, said second spectrum signal being obtained as a function of the wavelength by continuously varying the wavelength of the light emergent from said second spectroscopic means when the polarization directions of said first and second polarization means are set so as to intersect orthogonally to each other; means to find a third spectrum signal which is obtained as a function of the wavelength by continuously varying the wavelength of the light emergent from said second spectroscopic means when the polarization direction of said first polarization means is set different from those set for obtaining said first and second spectrum signals and when the polarization directions of said first and second polarization means are set identical; means to find a fourth spectrum signal which is obtained as a function of the wavelength by continuously varying the wavelength of the light emergent from said second spectroscopic means when the polarization direction of said first polarization means is set different from those set for obtaining said first and second spectrum signals and when the polarization directions of said first and second polarization means are set so as to intersect orthogonally to each other; and means to find an emission polarization spectrum as a function of the wavelength in response to the respective output signals from said means to form said ratio and said means to find said third and fourth spectrum signals.

Other objects and features of this invention will become more apparent from the following description taken with reference to the drawings.

DETAILED DESCRIPTION OF THE PREFERRED EMBODIMENTS

Before the detailed explanation of embodiments, the measuring principle of an emission polarization spectrum will be briefly described.

Under the state under which an excitation wavelength is fixed and under which the polarization direction of an excitation polarizer is set horizontal, the polarization direction of an emission polarizer is set horizontal, and the wavelengths of an emission monochromator are scanned, to obtain an emission or fluorescence spectrum $I_{HH}(\lambda_{EM})$ as a function of the wavelengths. Under the aforecited state, the polarization direction of the emission polarizer is set vertical, and the wavelengths of the emission monochromator are scanned, to obtain an emission or fluorescence spectrum $I_{HV}(\lambda_{EM})$ as a function of the wavelengths. From the emission spectra, a grating correction factor $G(\lambda_{EM})$ for correcting the polarization characteristics of the emission monochromator dependent upon the wavelengths is evaluated as a function of the wavelengths by the following expression and is stored and held:

$$G(\lambda_{EM}) = I_{HV}(\lambda_{EM})/I_{HH}(\lambda_{EM})$$

Subsequently, as the excitation wavelength remains fixed, the polarization direction of the excitation polarizer is changed-over from the horizontal direction to the vertical direction. While holding this state, likewise to the above the polarization direction of the emission polarizer is set horizontal and the wavelengths of the emission monochromator are scanned, to obtain an emission or fluorescence spectrum $I_{VH}(\lambda_{EM})$ as a function of the wavelengths and to evaluate an emission or fluorescence spectrum $G(\lambda_{EM}) \cdot I_{VH}(\lambda_{EM})$ corrected with the grating correction factor $G(\lambda_{EM})$.

Subsequently, under the aforecited state, the polarization direction of the emission polarizer is set at the same vertical direction as the polarization direction of the excitation polarizer, and the wavelengths of the emission monochromator are scanned, to obtain an emission or fluorescene spectrum $I_{VV}(\lambda_{EM})$ as a function of the wavelengths.

The emission polarization spectrum $P(\lambda_{EM})$ is evaluated as a function of the emission wavelengths by the following expression:

$$P(\lambda_{EM}) = \frac{I_{VV}(\lambda_{EM}) - G(\lambda_{EM}) \cdot I_{VH}(\lambda_{EM})}{I_{VV}(\lambda_{EM}) + G(\lambda_{EM}) I_{VH}(\lambda_{EM})}$$

Hereunder, an embodiment of this invention will be described in detail with reference to the drawings.

Figure 1:
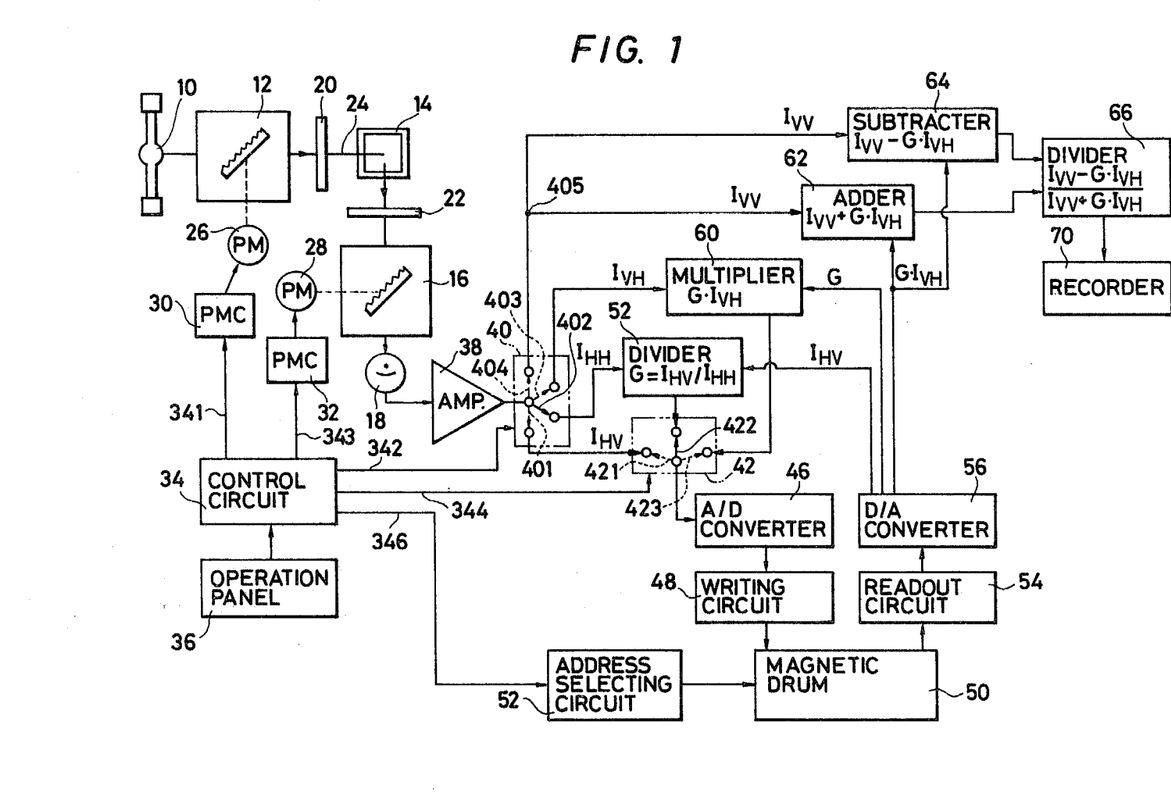
FIG. 1 is a block diagram of an embodiment of a spectrofluorometer according to this invention.

Referring to FIG. 1, light from a light source 10 is separated into spectral components in an excitation monochromator 12, and a fluorescent sample 14 is irradiated by the resulting monochromatic excitation light. Fluorescence is emitted from the fluorescent sample 14, and is separated into spectral components in an emission monochromator 16 arranged in a direction orthogonal to the irradiation direction of the monochromatic excitation light. The resulting light is received by a sensor 18 and is photoelectrically converted. The monochromatic excitation light and the fluorescence are caused to emerge as lights made up of polarization components in specified directions, by means of an excitation polarizer 20 and an emission polarizer 22 which are respectively arranged between the excitation monochromator 12 and the fluorescent sample 14 and between the fluorescent sample 14 and the emission monochromator 16. The wavelength shafts of the excitation monochromator 12 and the emission monochromator 16 are respectively connected with pulse motors 26 and 28, which in turn are respectively connected with a control circuit 34 through pulse motor controllers 30 and 32. The control circuit 34 is connected with an operation panel 36 for transmitting the instructions of an operator to the control circuit 34.

Now, an embodiment of the spectrofluorometer according to this invention will be described in conformity with the operating procedures of the measurement of an emission polarization spectrum.

The fluorescent sample 14 is set, and the polarization direction of the excitation polarizer 20 is set at the horizontal direction, while the polarization direction of the emission polarizer 22 is set at the vertical direction orthogonal thereto. When, under this state, the instruction of a first measurement mode is given to the operation panel 36, the control circuit 34 provides control signals 341 and 343, on the basis of which the excitation monochromator 12 has the position of its grating fixed so as to cause light of a predetermined wavelength to emerge and the emission monochromator 16 has its grating driven and is subjected to the wavelength scanning by means of the pulse motor controller 32 and the pulse motor 28. The first spectrum signal $I_{HV}(\lambda_{EM})$ based on the wavelength emergent from the emission monochromator 16 is received by the sensor 18.

The received signal of the sensor 18 is amplified by an amplifier 38, whereupon the amplified signal is led to an A/D converter 46 through first and second change-over switches 40 and 42 which are respectively set at first switching positions 401 and 421 by control signals 342 and 344 from the control circuit 34 based on the first measurement mode command signal. The resulting signal after the A/D conversion of the A/D converter 46 is applied through a writing circuit 48 to a magnetic drum 50 and is stored therein. An address selecting signal 346 from the control circuit 34 is applied to the magnetic drum 50 through an address selecting circuit 52, so that the signal applied to the magnetic drum 50 is addressed to a predetermined position.

Subsequently, the polarization direction of the emission polarizer 22 is set at the same direction as the polarization direction of the excitation polarizer 20, that is, at the horizontal direction, and a command signal of a second measurement mode is given to the control circuit 34 through the operation panel 36. Then, likewise to the first measurement mode, the wavelength scanning is executed in the emission monochromator 16 through the pulse motor controller 32 as well as the pulse motor 28 on the basis of the control signal 343 for driving the fluorescence wavelength. The second spectrum signal $I_{HH}(\lambda_{EM})$ based on the scanning wavelength emergent from the emission monochromator 16 is received by the sensor 18 and is photoelectrically converted. The second spectrum signal after the photoelectric conversion is amplified by the amplifier 38. The amplified signal is applied to a divider 58 through the change-over switch 40 which is now changed-over to and set at a switching position 402 by the control signal 342 from the control circuit 34 based on the second measurement mode command signal. Simultaneously therewith, the first spectrum signal $I_{HV}(\lambda_{EM})$ having been stored in the magnetic drum 50 is read out from the magnetic drum 50 by a readout circuit 54, and it is applied to the divider 58 through a D/A converter 56. The divider 58 forms the signal $G(\lambda_{EM})$ representative of the ratio between the first spectrum signal $I_{HV}(\lambda_{EM})$ and the second spectrum signal $I_{HH}(\lambda_{EM})$, that is, it forms $I_{HV}(\lambda_{EM})/I_{HH}(\lambda_{EM})=G(\lambda_{EM})$.

The signal $G(\lambda_{EM})$ obtained in the divider 58 represents the ratio of the spectrum signals which are obtained by the wavelength scannings of the emission monochromator 16 at the time when the wavelength of the excitation monochromator 12 is fixed, the polarization direction of the excitation polarizer 20 is fixed to the horizontal direction and the polarization direction of the emission polarizer 22 is made the same as and orthogonal to the polarization direction of the excitation polarizer 20. This signal $G(\lambda_{EM})$ is the grating correction factor corresponding to the wavelength as serves to correct the polarization characteristics based on the wavelength of the emission monochromator 16.

The output signal $G(\lambda_{EM})=I_{HV}(\lambda_{EM})/I_{HH}(\lambda_{EM})$ from the divider 58 is applied to the A/D converter 46 through the change-over switch 42 which is now changed-over to and set at a second switching position 422 by the control signal 344 from the control circuit 34 based on the second measurement mode command signal. Further, the resulting signal is stored and held in a predetermined position of the magnetic drum 50 through the writing circuit 48. At this time, an address selecting signal is applied from the control circuit 34 through the address selecting circuit 52 to the magnetic drum 50.

Subsequently, under the state under which the polarization direction of the excitation polarizer 20 is changed-over from the horizontal direction to the vertical direction and is fixed to the latter and under which the polarization of the emission polarizer 22 is set at the horizontal direction, a command signal of a third measurement mode is applied to the control circuit 34 through the operation panel 36. Then, similarly to the above, the wavelength scanning of the emission monochromator 16 is performed with the wavelength driving control signal 343 from the control circuit 34. The third spectrum signal $I_{VH}(\lambda_{EM})$ based on the wavelength caused to emerge from the emission monochromator 16 by the wavelength scanning of the emission monochromator 16 is received by the sensor 18. This third spectrum signal $I_{VH}(\lambda_{EM})$ is applied to a multiplier 60 through the amplifier 38 and the change-over switch 40 which is now changed-over to and set at a third switching position 403 by the control signal 342 from the control circuit 34 based on the third measurement mode command signal. Simultaneously therewith, the grating correction factor signal $G(\lambda_{EM})$ having been stored and held in the magnetic drum 50 is read out from the magnetic drum 50 by the readout circuit 54, and it is applied to the multiplier 60 through the D/A converter 56.

The multiplier 60 forms a signal $G(\lambda_{EM})\cdot I_{VH}(\lambda_{EM})$ representative of the product between the third spectrum signal $I_{VH}(\lambda_{EM})$ and the grating correction factor signal $G(\lambda_{EM})$, to make the correction of the third spectrum signal $I_{VH}(\lambda_{EM})$.

The output signal $G(\lambda_{EM})\cdot I_{VH}(\lambda_{EM})$ of the multiplier 60 is applied to the A/D converter 46 through the change-over switch 42 which is now changed-over to and set at a third switching position 423 by the control signal 344 from the control circuit 34 based on the third measurement mode command signal. Further, the resulting signal is applied through the writing circuit 48 to the magnetic drum 50 and is stored and held in a predetermined position thereof.

Subsequently, as the polarization direction of the excitation polarizer 20 remains fixed to the vertical direction, the polarization direction of the emission polarizer 22 is changed-over from the horizontal direction to the vertical direction and is set at the latter. When, under this state, a fourth measurement mode command signal is applied to the control circuit 34 through the operation panel 36, the wavelength scanning of the emission monochromator 16 is executed by the wavelength driving control signal 343 from the control circuit 34 similarly to the above. The fourth spectrum signal $I_{VV}(\lambda_{EM})$ based on the wavelength from the emission monochromator 16 is applied to an adder 62 and also a subtracter 64 through the sensor 18, the amplifier 38, the change-over switch 40 which is now changed-over to and set at a fourth switching position 404 by the control signal 342 from the control circuit 34 based on the fourth measurement mode command signal, and a branch point 405. Simultaneously therewith, the corrected third spectrum signal $G(\lambda_{EM})\cdot I_{VH}(\lambda_{EM})$ having been stored and held in the magnetic drum 50 is read out from the magnetic drum 50 by the readout circuit 54, and it is applied to the adder 62 and also the subtractor 64 through the D/A converter 56 as well as a branch point 562.

The adder 62 forms a signal representative of the sum between the fourth spectrum signal $I_{VV}(\lambda_{EM})$ and the corrected third spectrum signal $G(\lambda_{EM})\cdot I_{VH}(\lambda_{EM})$, that is, a signal $I_{VV}(\lambda_{EM}) + G(\lambda_{EM})\cdot I_{VH}(\lambda_{EM})$.

On the other hand, the subtracter 64 forms a signal representative of the difference between the fourth spectrum signal $I_{VV}(\lambda_{EM})$ and the corrected third spectrum signal $G(\lambda_{EM})I_{VH}(\lambda_{EM})$, that is, a signal $I_{VV}(\lambda_{EM}) - G(\lambda_{EM})\cdot I_{VH}(\lambda_{EM})$.

The respective output signals $\{I_{VV}(\lambda_{EM})+G(\lambda_{EM})\cdot I_{VH}(\lambda_{EM})\}$ $\{I_{VV}(\lambda_{EM})-G(\lambda_{EM})\cdot I_{VH}(\lambda_{EM})\}$ of the adder 62 and the subtractor 64 are applied to a divider 66, which forms a signal representative of the ratio of the applied signals, that is, a signal given by:

$$\frac{I_{VV}(\lambda_{EM}) - G(\lambda_{EM}) \cdot I_{VH}(\lambda_{EM})}{I_{VV}(\lambda_{EM}) + G(\lambda_{EM}) \cdot I_{VH}(\lambda_{EM})}$$

This signal obtained by the divider 66 is a signal which represents the emission polarization spectrum of the fluorescent sample 14 used for the measurement. The emission polarization spectrum is recorded by a recorder 70.

As understood from the above description, according to the embodiment of this invention, the polarization characteristics based on the wavelength of the emission monochromator 16 can be corrected by the simple construction. This brings forth the advantage that the measurement of the emission polarization spectrum having hitherto been deemed difficult or impossible can be made precisely and simply.

In the construction of the above embodiment, also the excitation polarization spectrum having hitherto been measured can be obtained in such a way that control signals for fixing the wavelength of the emission monochromator 16 and performing the wavelength scanning of the excitation monochromator 12 are respectively applied to the pulse motors 26 and 28 through the pulse motor controllers 30 and 32 from the control circuit 34.

Accordingly, this invention realizes the spectrofluorometer which permits a wider range of analyses at a higher precision as compared with the prior-art spectrofluorometer.

Figure 2:
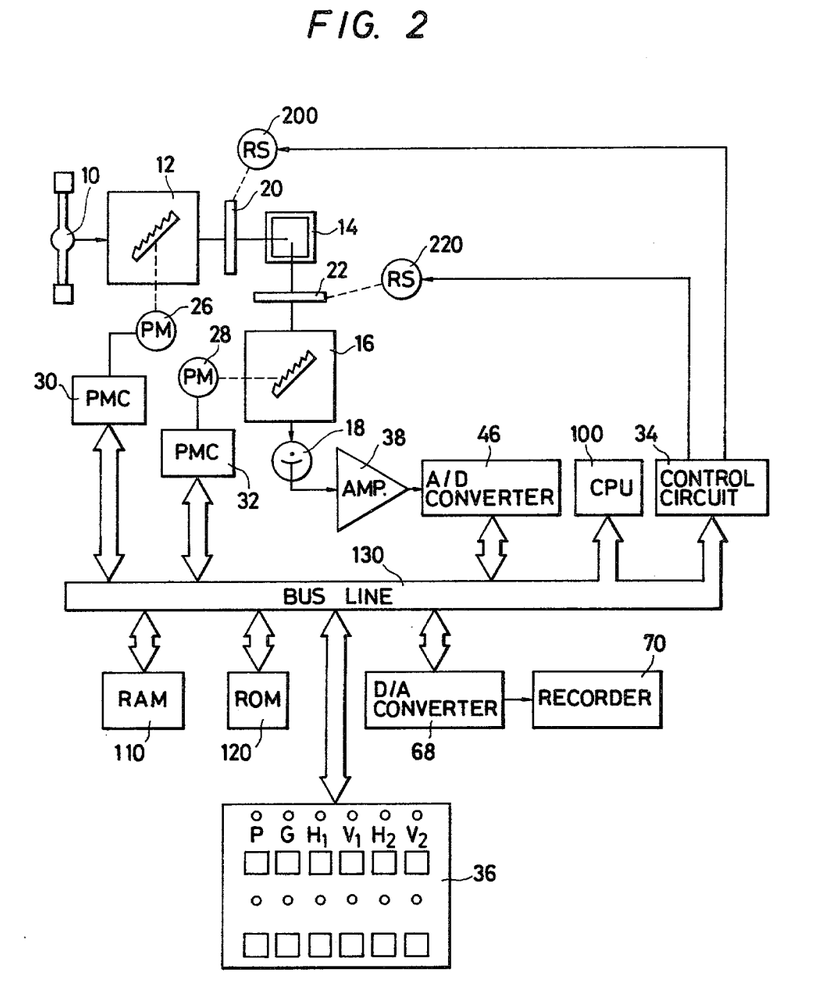
FIG. 2 is a block diagram of another embodiment of the spectrofluorometer according to this invention.

FIG. 2 shows the construction of another embodiment of the spectrofluorometer according to this invention. In this embodiment, the analog construction of the spectrofluorometer shown in FIG. 1 is modified into a digital construction by introducing a microcomputer. Constituents having the same reference numerals as in FIG. 1 have the same designations and the same functions.

The point of difference of the construction of FIG. 2 from that of FIG. 1 is that data and control signals are transmitted among the microcomputer 100, the control circuit 34, a RAM 110, a ROM 120, the operation panel 36, etc. through a bus line 130.

Figure 3:
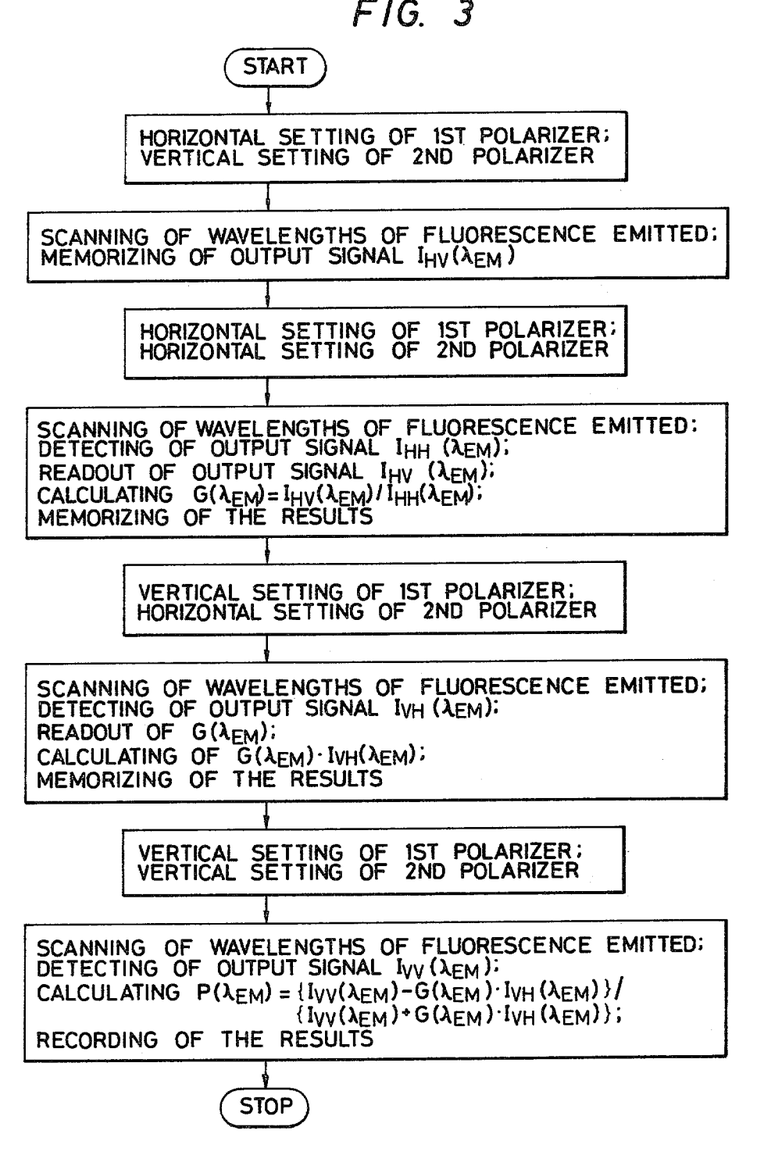
FIG. 3 is a flow chart which indicates the operating procedures of the apparatus shown in FIG. 2.

In the construction of FIG. 2, a program based on a flow chart shown in FIG. 3 is written in the ROM 120.

A series of operations such as predetermined arithmetic processings in the CPU 100 and operations of storing data into the RAM 110 are carried out with command signals from the operation panel 36 to be transmitted through the bus line 130.

An example of measurement of an emission polarization spectrum according to the embodiment of this invention shown in FIG. 2 will be described in accordance with the flow chart given in FIG. 3.

When operation keys on the operation panel 36 as indicated by G, H1 and V2 in FIG. 2 are depressed by an operator in order to instruct the first measurement mode, the command signals are transmitted to the control circuit 34 through the bus line 130. The control circuit 34 provides control signals in conformity with the program set in the ROM 120. The control signals from the control circuit 34 energize a rotary solenoid 200 for driving the excitation polarizer 20 and a rotary solenoid 220 for driving the emission polarizer 22, respectively. Thus, the excitation polarizer 20 is set so that the polarization direction thereof may be horizontal, while the emission polarizer 22 is set so that the polarization direction thereof may be vertical. Subsequently, upon command signals from the ROM 120, the control signals from the control circuit 34 are applied to the pulse motor controllers 30 and 32 through the bus line 130. Thus, the pulse motor 26 is controlled so that the excitation monochromator 12 may select a predetermined excitation wavelength. In addition, the pulse motor 28 is controlled so that wavelengths may be scanned in the emission monochromator 16.

The first spectrum signal $I_{HV}(\lambda_{EM})$ obtained by the wavelength scanning of the emission monochromator 16 and concerning the polarization characteristics of the emission monochromator 16 is stored and held in a predetermined address of the RAM 110 through the sensor 18, the amplifier 38, the A/D converter 46 and the bus line 130 on the basis of the command signal from the ROM 120.

Subsequently, when the operator depresses operation keys G, H1 and H2 on the operation panel 36 in order to instruct the second measurement mode, the command signals are applied to the control circuit 34 through the bus line 130. Control signals are fed from the control circuit 34 to the rotary solenoids 200 and 220 in accordance with the program set in the ROM 120, to make the control of changing-over only the polarization direction of the emission polarizer 22 from the vertical direction to the horizonal direction. Subsequently, the control signal from the control circuit 34 is applied to the pulse motor controller 32 through the bus line 130, and the wavelength scanning of the emission monochromator 16 is performed. The second spectrum signal $I_{HH}(\lambda_{EM})$ obtained by the wavelength scanning of the emission monochromator 16 and concerning the polarization characteristics of the emission monochromator 16 is received by the sensor 18. This second spectrum signal $I_{HH}(\lambda_{EM})$ is applied to the microcomputer 100 through the amplifier 38, the A/D converter 46 and the bus line 130. Simultaneously therewith, the first spectrum signal $I_{HV}(\lambda_{EM})$ is read out from the RAM 110 and applied to the CPU 100 through the bus line 130 on the basis of a command signal from the ROM 120. In the CPU 100, the operation of $I_{HV}(\lambda_{EM})/I_{HH}(\lambda_{EM})=G(\lambda_{EM})$ is executed on the basis of a command signal of the ROM 120. The operated result of the CPU 100 is applied to the RAM 110 through the bus line 130 and is stored and held in a predetermined address.

Subsequently, when the operator depresses operation keys P, V1 and H2 on the operation panel 36 in order to instruct the third measurement mode, the command signals are applied to the control circuit 34 through the bus line 130. Control signals are fed from the control circuit 34 to the rotary solenoids 200 and 220 in accordance with the program set in the ROM 120, to set the excitation polarizer 20 so that its polarization direction may become the vertical direction and to set the emission polarizer 22 so that its polarization direction may become the horizontal direction. Next, the control signal from the control circuit 34 is transmitted to the pulse motor controller 32 through the bus line 130, and the wavelength scanning of the emission monochromator 16 is performed. The third spectrum signal $I_{VH}(\lambda_{EM})$ emerging from the emission monochromator 16, received by the sensor 18 and concerning the polarization characteristics of the sample is applied to the CPU 100 through the amplifier 38, the A/D converter 46 and the bus line 130. Simultaneously, the grating correction factor signal $G(\lambda_{EM})=I_{HV}(\lambda_{EM})/I_{HH}(\lambda_{EM})$ having been stored in the RAM 110 is read out in accordance with the program of the ROM 120 and is applied to the CPU 100 through the bus line 130. The CPU 100 executes the operation of correcting the third spectrum signal $I_{VH}(\lambda_{EM})$ concerning the polarization characteristics of the sample, by the use of the grating correction factor signal $G(\lambda_{EM})$ formed from the ratio of the first and second spectrum signals $I_{HV}(\lambda_{EM})$ and $I_{HH}(\lambda_{EM})$ concerning the polarization characteristics of the emission monochromator 16, and it provides the corrected signal $G(\lambda_{EM}) \cdot I_{VH}(\lambda_{EM})$ as its output signal. This corrected signal $G(\lambda_{EM}) \cdot I_{VH}(\lambda_{EM})$ is applied to the RAM 110 through the bus line 130 and is stored and held in a predetermined address.

Subsequently, when the operator depresses operation keys P, V1 and V2 on the operation panel 36 to instruct the fourth measurement mode, control signals for energizing the rotary solenoids 200 and 220 are fed from the control circuit 34 on the basis of a command signal from the ROM 120, whereby the excitation polarizer 20 and the emission polarizer 22 are set so that the polarization direction of the former may become the vertical direction and that the polarization direction of the latter may become the vertical direction. Next, the wavelength scanning of the emission monochromator 16 is executed on the basis of the control signal from the control circuit 34 similarly to the foregoing. The fourth spectrum signal $I_{VV}(\lambda_{EM})$ emerging from the emission monochromator 16, received by the sensor 18 and concerning the polarization characteristics of the sample is applied to the CPU 100 through the amplifier 38, the A/D converter 46 and the bus line 130. Simultaneously, the corrected spectrum signal $I_{VH}(\lambda_{EM}) \cdot G(\lambda_{EM})$ having been stored and held in the RAM 110 is read out in accordance with the ROM 120 and is applied to the CPU 100 through the bus line 130.

The CPU 100 executes an operation based on the following expression:

$$\frac{I_{VV}(\lambda_{EM}) - G(\lambda_{EM}) \cdot I_{VH}(\lambda_{EM})}{I_{VV}(\lambda_{EM}) + G(\lambda_{EM}) \cdot I_{VH}(\lambda_{EM})} = P(\lambda_{EM})$$

The result obtained is applied to the recorder 70 through the bus line 130 as well as the D/A converter 68 and indicated as the signal $P(\lambda_{EM})$ representative of the emission polarization spectrum found.

According to the modified embodiment of this invention constructed as above described, the series of measurement operations are carried out in accordance with the predetermined program in interlocking with the microcomputer 100. Therefore, the whole apparatus become compact, and a simple and prompt measurement is realized.

Also in the modified embodiment, the excitation polarization spectrum can be similarly obtained by fixing the emission wavelength and subjecting the excitation wavelengths to the scanning as stated previously.

Thus, according to this invention, not only the excitation polarization spectrum but also the emission polarization spectrum can be measured, which brings forth the advantage that the range of analyses is expanded more than in the prior-art apparatus.

Figure 4:
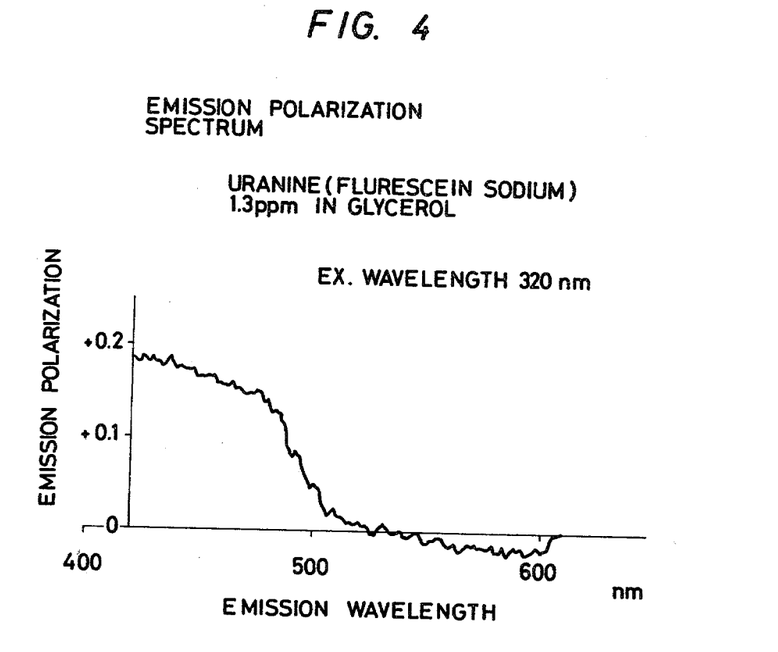
FIG. 4 illustrates an example of measurement of an emission polarization spectrum obtained with the spectrofluorometer according to this invention.

FIG. 4 shows an example of measurement of the emission polarization spectrum of Uranine (fluorescein sodium) 1.3 ppm in Glycerol as has been obtained at an excitation wavelength of 320 nm by means of the spectrofluorometer according to this invention. In the graph of FIG. 4, the axis of ordinates represents the emission polarization, and the axis of abscissas the emission wavelength (in nm). As seen from FIG. 4, the background fluorescence (B) and the fluorescence (A) from the uranine are definitely distinguished with the boundary at the vicinity of a wavelength of 500 nm. Thus, the presence of uranine in the sample can be readily recognized.

We claim:

1. A spectrofluorometer comprising first spectroscopic means to separate light from a light source into its spectral components; second spectroscopic means to separate fluorescence into its spectral components, the fluorescence being emitted from a measurement sample by irradiating it with monochromatic light from said first spectroscopic means; wavelength drive means to perform wavelength scannings of said first and second spectroscopic means; control means to control said wavelength drive means; first and second polarization means to polarize lights, said means being respectively arranged between said first spectroscopic means and said measurement sample and between said measurement sample and said second spectroscopic means, said first and second polarization means have their polarization direction controlled by said control means; sensing means to sense light emergent from said second spectroscopic means; first signal processing means to form a signal representative of a ratio between a first spectrum signal and a second spectrum signal, the first spectrum signal being obtained by a wavelength scanning of said second spectroscopic means when said first and second polarization means are arranged so that polarization directions of lights emergent from said first and second polarization means are identical, the second spectrum signal being obtained by a wavelength scanning of said second spectroscopic means when said first and second polarization means are arranged so that the polarization directions of the lights emergent from said first and second polarization means intersect orthogonally to each other; second signal processing means to correct a third spectrum signal in response to the output signal from said first signal processing means, the third spectrum signal being obtained by a wavelength scanning of said second spectroscopic means when said first and second polarization means are arranged so that the polarization direction of the light emergent from said first polarization means is a direction different from those in which said first and second spectrum signals have been obtained and that the polarization directions of the lights emergent from said first and second polarization means intersect orthogonally to each other; and third signal processing means to form a signal representative of an emission polarization spectrum of said measurement sample from a fourth spectrum signal and an output signal from said second signal processing means, the fourth spectrum signal being obtained by a wavelength scanning of said second spectroscopic means when said first and second polarization means are arranged so that the polarization direction of the light emergent from said first polarization means is a direction different from those in which said first and second spectrum signals have been obtained and that the polarization directions of the lights emergent from said first and second polarization means are identical.

2. A spectrofluorometer as defined in claim 1, comprising signal storage means to store and hold the respective output signal from said first signal processing means and said second signal processing means.

3. A spectrofluorometer as defined in claim 1 or 2, comprising control means to control said wavelength drive means.

4. A spectrofluorometer comprising first spectroscopic means to separate light from a light source into its spectral components; second spectroscopic means to separate fluorescence into its spectral components, the fluorescence being emitted from a measurement sample by irradiating it with monochromatic light from said first spectroscopic means; wavelength driving means to scan wavelengths of said first and second spectroscopic means; first and second polarization means to polarize lights, said means being respectively arranged between said first spectroscopic means and said measurement sample and between said measurement sample and said second spectroscopic means; first and second polarization direction positioning means to position said polarization directions of said first and second polarization means; control means to control said first and second polarization means respectively in accordance with a predetermined program; sensing means to sense light emergent from said second spectroscopic means; and means to operate and process an emission polarization spectrum $P(\lambda)$ in accordance with the following expression:

$$P(\lambda) = \frac{I_4(\lambda) - I_3(\lambda) \cdot I_2(\lambda)/I_1(\lambda)}{I_4(\lambda) + I_3(\lambda) \cdot I_2(\lambda)/I_1(\lambda)}$$

from a first spectrum signal $I_1(\lambda)$ which is obtained by a wavelength scanning of said second spectroscopic means when said first and second polarization means are arranged so that polarization directions of lights emergent from said first and second polarization means are identical, a second spectrum signal $I_2(\lambda)$ which is obtained by a wavelength scanning of said second spectroscopic means when said first and second polarization means are arranged so that the polarization directions of the lights emergent from said first and second polarization means intersect orthogonally to each other, a third spectrum signal $I_3(\lambda)$ which is obtained by a wavelength scanning of said second spectroscopic means when said first and second polarization means are arranged so that the polarization direction of the light emergent from said first polarization means is different from those at the obtainments of said first and second spectrum signals and that the polarization directions of the lights emergent from said first and second polarization means intersect orthogonally to each other, and a fourth spectrum signal $I_4(\lambda)$ which is obtained by a wavelength scanning of said second spectroscopic means when said first and second polarization means are arranged so that the polarization direction of the light emergent from said first polarization means is different from those at the obtainments of said first and second spectrum signals and that the polarization directions of the lights emergent from said first and second polarization means are identical.

5. A spectrofluorometer as defined in claim 4, comprising storage means to store said spectrum signal obtained by the wavelength scannings of said second spectroscopic means and the output signal of the operating and processing means, and control means to control the input and output signals of said storage means and said operating and processing means in accordance with a predetermined program.

6. A spectrofluorometer comprising an excitation monochromator which separates light from a light source into its spectral components; an emission monochromator which separates fluorescence into its spectral components, the fluorescence being emitted from a measurement sample by irradiating it with monochromatic light from said excitation monochromator; first and second polarizers for polarizing lights, said polarizers being respectively arranged between said excitation monochromator and said measurement sample and between said measurement sample and said emission monochromator; a sensor which senses light emergent from said emission monochromator; first and second pulse motors which are respectively coupled to wavelength shafts of said excitation monochromator and said emission monochromator; first and second pulse motor controllers which control said first and second pulse motors respectively; first and second rotary solenoids which are respectively coupled to said first and second polarizers and which set polarization directions of said first and second polarizers into predetermined directions respectively; an A/D converter which subjects an output signal of said sensor to an A/D conversion; a microcomputer which is connected with said A/D converter through a bus line and which operates and processes output signals of said A/D converter in predetermined procedures; a program unit which commands said microcomputer through said bus line to follow the predetermined procedures; storage device which is connected with said A/D converter and said microcomputer through said bus line and which store output signals thereof; a control circuit which is connected with said program unit through said bus line and which gives control signals to said first and second pulse motor controllers and said first and second rotary solenoids; a D/A converter which is connected with said microcomputer through said bus line and which subjects the output signal from said microcomputer to a D/A conversion; and a recorder which indicates an output signal of said D/A converter; an emission polarization spectrum $P(\lambda_{EM})$ being found in accordance with the following expression:

$$P(\lambda_{EM}) = \frac{I_{VV}(\lambda_{EM}) - G(\lambda_{EM}) \cdot I_{VH}(\lambda_{EM})}{I_{VV}(\lambda_{EM}) + G(\lambda_{EM}) \cdot I_{VH}(\lambda_{EM})}$$

from a signal $G(\lambda_{EM})=I_{HV}(\lambda_{EM})/I_{HH}(\lambda_{EM})$ which represents a ratio between a spectrum signal $I_{HV}(\lambda_{EM})$ and a spectrum signal $I_{HH}(\lambda_{EM})$, the former spectrum signal being obtained by the wavelength scanning of said emission monochromator when said first polarizer is arranged so that the polarization direction of excitation light to emerge therefrom is horizontal and said second polarizer is arranged so that the polarization direction of fluorescence to emerge therefrom is vertical, the latter spectrum signal being obtained by the wavelength scanning of said emission monochromator when with the polarization direction of said first polarizer held horizontal the polarization direction of said second polarizer is made horizontal, a spectrum signal $I_{VH}(\lambda_{EM})$ which is obtained by the wavelength scanning of said emission monochromator when said first polarizer is arranged so that the polarization direction of the excitation light to emerge therefrom is vertical and said second polarizer is arranged so that the polarization direction of the fluorescence to emerge therefrom is horizontal, and a spectrum signal $I_{VV}(\lambda_{EM})$ which is obtained by the wavelength scanning of said emission monochromator when with the polarization direction of said first polarizer held vertical the polarization direction of said second polarizer is made vertical.

7. A spectrofluorometer comprising an excitation monochromator which separates light from a light source into its spectral components; an emission monochromator which separates fluorescence into its spectral components, the fluorescence being emitted from a measurement sample by irradiating it with monochromatic light from said excitation monochromator; first and second polarizers for polarizing lights, said polarizers being respectively arranged between said excitation monochromator and said measurement sample and between said measurement sample and said emission monochromator; a sensor which senses light emergent from said emission monochromator; wavelength driving mechanisms which are respectively coupled to wavelength shafts of said excitation monochromator and said emission monochromator and which scan wavelengths of the respective monochromators; first and second polarization direction means to position said polarization directions of said first and second polarization means; a storage device which holds a spectrum signal $I_{HV}(\lambda_{EM})$ obtained by the wavelength scanning of said emission monochromator when said first polarizer is arranged so that a polarization direction of excitation light to emerge therefrom is horizontal and said second polarizer is arranged so that a polarization direction of fluorescence to emerge therefrom is vertical; a divider unit which receives a spectrum signal $I_{HH}(\lambda_{EM})$ obtained by the wavelength scanning of said emission monochromator when without changing the polarization direction of said first polarizer said second polarizer is arranged so that the polarization direction of the fluorescence to emerge therefrom is horizontal and also the spectrum signal $I_{HV}(\lambda_{EM})$ having been held in said storage device, said divider unit forming a signal $G(\lambda_{EM})=I_{HV}(\lambda_{EM})/I_{HH}(\lambda_{EM})$ representative of a ratio between the received spectrum signals, an output terminal of said divider unit being connected to an input terminal of said storage device; a multiplier unit which receives a spectrum signal $I_{VH}(\lambda_{EM})$ obtained by the wavelength scanning of said emission monochromator when said first polarizer is arranged so that the polarization direction of the excitation light to emerge therefrom is vertical and said second polarizer is arranged so that the polarization direction of the fluorescence to emerge therefrom is horizontal and also the signal $G(\lambda_{EM})$ representative of the ratio having been held in said storage device, said multiplier unit forming a signal $G(\lambda_{EM})\cdot I_{VH}(\lambda_{EM})$ representative of a product between the received signals, an output terminal of said multiplier unit being connected to the input terminal of said storage device; an adder unit and a subtracter unit both of which receive a spectrum signal $I_{VV}(\lambda_{EM})$ obtained by the wavelength scanning of said emission monochromator when without changing the polarization direction of said first polarizer said second polarizer is arranged so that the polarization direction of the fluorescence to emerge therefrom is vertical and also the output signal $G(\lambda_{EM})\cdot I_{VH}(\lambda_{EM})$ of said multiplier unit having been held in said storage device, said adder unit and said subtracter unit respectively forming a signal $I_{VV}(\lambda_{EM})+G(\lambda_{EM})\cdot I_{VH}(\lambda_{EM})$ and a signal $I_{VV}(\lambda_{EM})-G(\lambda_{EM})\cdot I_{VH}(\lambda_{EM})$ representative of a sum and a difference between the received signals; and a divider unit which forms a signal $$\frac{I_{VV}(\lambda_{EM}) - G(\lambda_{EM}) \cdot I_{VH}(\lambda_{EM})}{I_{VV}(\lambda_{EM}) + G(\lambda_{EM}) \cdot I_{VH}(\lambda_{EM})}$$

representative of a ratio between the respective output signals of said adder unit and said subtracter unit.

* * * * *